United States Patent [19]
Horres, Jr.

[11] Patent Number: 5,368,571
[45] Date of Patent: Nov. 29, 1994

[54] ELECTROCHEMICAL CONTROLLED DISPENSING ASSEMBLY AND METHOD

[75] Inventor: Charles R. Horres, Jr., Del Mar, Calif.

[73] Assignee: Pharmetrix Corporation, Menlo Park, Calif.

[21] Appl. No.: 190,639

[22] Filed: Feb. 1, 1994

Related U.S. Application Data

[63] Continuation-in-part of Ser. No. 12,876, Feb. 3, 1993, Pat. No. 5,290,240.

[51] Int. Cl.$^5$ .............................................. A61M 37/00
[52] U.S. Cl. ................................. 604/131; 604/141; 604/133; 128/DIG. 12
[58] Field of Search ................ 128/DIG. 12, DIG. 13, 128/898; 604/49, 51, 131, 133, 134, 140, 141, 890.1, 891.1

[56] References Cited

U.S. PATENT DOCUMENTS

| | | | |
|---|---|---|---|
| 4,687,423 | 8/1987 | Maget | 417/379 |
| 4,874,500 | 10/1989 | Madou | 204/412 |
| 4,886,514 | 12/1989 | Maget | 604/891.1 |
| 4,902,278 | 2/1990 | Maget et al. | 604/145 |
| 5,090,963 | 2/1992 | Gross | 604/132 |
| 5,223,265 | 6/1993 | Wong | 424/473 |

OTHER PUBLICATIONS

Espenscheid, Mark W. and Martin, Charles R. "Electroactive Ion Exchange Polymers", *J. Electroanal. Chem.* 188 (1985) pp. 73–84.

McCarty, Lyle H. "A Valve on a Chip!," *Design News,* Jan. 20, 1992, pp. 111–112.

*Primary Examiner*—C. Fred Rosenbaum
*Assistant Examiner*—Michael Rafa
*Attorney, Agent, or Firm*—Townsend & Townsend Khourie & Crew

[57] ABSTRACT

A pump assembly (20) employs electrochemistry to selectively control the delivery rate of a dispensing fluid (21) from a dispensing reservoir (24) by selectively controlling the flow rate of a driving fluid (19) from a driving reservoir (23) to a receiving reservoir (33). A partition (25), separating the driving reservoir from the receiving fluid reservoir, includes at least one aperture (28) which is opened or closed depending upon an electrical signal from a remote programming unit. Flow into the receiving reservoir deflects a barrier member to expel dispensing fluid from the dispensing reservoir. The dispensing fluid flow rate can be programmed to provide an appropriate steady or varying flow rate; user-initiated pulses of dispensing fluid can also be provided. A method of controlled infusion of an infusate employing electrochemistry is also provided.

4 Claims, 4 Drawing Sheets

ELECTROCHEMICAL CONTROLLED DISPENSING ASSEMBLY AND METHOD

CROSS REFERENCE TO RELATED APPLICATION

This application is a continuation-in-part of Ser. No. 08/012 876, filed Feb. 3, 1993 U.S. Pat. No. 5,290,240, the disclosure of which is incorporated by reference.

BACKGROUND OF THE INVENTION

The present invention relates, generally, to fluid dispensing assemblies and, more particularly, to electrochemical controlled disposable dispensing assemblies for medicament dispensing.

Fluid or medicament infusion programs are generally preferred to single or multiple injection programs in that the delivery rate of infusate can be controlled to a greater degree over a period of time. Typically, the infusate is topically administered directly onto the skin, wound site or eyes or is injected under the skin or directly into the vascular system or muscular tissue. In particular, continuous delivery parenteral drug therapy is most preferred because the controlled delivery of the medicament reduces toxic or other side effects associated with sharp pulses of the medicament, significantly improves the effectiveness of the therapy program, and increases patient comfort.

Broadly, an infusion device includes a container providing a reservoir of medicament or infusate coupled to a tube having a dispensing channel or the like. The tube includes a dispensing end which communicates directly with the recipient. Disposed in the fluid path between the dispensing end and the reservoir is a regulating device which controls the flow rate of the infusate through the channel.

The traditional and simplest infusion device for delivering sustained parenteral treatments is an intravenous drip apparatus which employs gravity to move the infusate from the reservoir through the channel and into the patient. The regulating device is often provided by a restrictor in the form of a roller clamp physically acting on an exterior surface of the tube which restricts the flow through the dispensing channel. One problem with these roller clamp restrictors, however, is that they are gravimetrically dependent on the hydrostatic pressure of the infusate formed at the roller clamp. Hence, the roller clamp cannot accurately regulate the dispensing flow because as the pressure head of the infusate decreases, the hydrostatic pressure decreases which proportionately reduces the flow rate of the infusate through the roller clamp.

To overcome this problem, electronic regulation devices were developed to replace the roller clamp restrictors. These electronic devices are capable of electronically sensing the flow rate through the channel and automatically adjusting the restriction area of flow through internal adjusters to maintain the desired infusion rate. While these devices have improved the accuracy of intravenous drip apparatus, they are burdensome and impractical since the dispensing reservoir must be positioned above the recipient at all times to create the proper pressure head at the electronic regulation device.

More advanced infusion systems have been developed which actively pump the infusate into the patient rather than relying on gravimetric infusion. Typically, a piston, plunger or the like is urged or advanced into a fixed volume dispensing reservoir containing the infusate which positively displaces the infusate and expels it from the reservoir. Examples of these infusion pumps include syringe pumps, reciprocating piston pumps and peristaltic pumps.

The driving forces displacing the piston or plunger are generally provided by spring elements, chemical systems or electric resources. The most common driving force, however, is that provided by an electric motor which is capable of controlling the infusate flow rate from the dispensing reservoir. Hence, the flow rate of the medicament or pharmaceutical agent suspended in the infusate can be customized to the particular needs of the patient more accurately than the intravenous drip apparatus.

While these above-mentioned intravenous drip apparatuses and infusion pumps are perfectly acceptable in a hospital environment, neither are ambulatory which severely restricts the activity of the recipient. Hence, considerable research has been devoted to the development of small disposable and portable infusion pumps of the positive displacement nature. Electronic powered delivery means or the like would provide a more selectable driving force to control the expulsion of the infusate from the dispensing reservoir but would not be suitable for a disposable product because of the inherent increased costs and weight. Therefore, these newly developed disposable infusion pumps generally utilize springs, vapor pressure or elastomeric balloons as a source of driving or displacement energy to expel the infusate from the dispensing reservoir.

Due in part to the uncontrolled nature of these sources of driving energy, typically, a flow regulation internal restrictor is included in the fluid flow path between the infusion pump and the dispensing end. These restrictors are generally precision bore tubing elements or filter elements which impede the flow of the infusate through the fluid channel. Discrete value flow rate restrictors are available to incorporate in the fluid path to selectively establish infusate flow rate. Typical of these portable infusion pumps are disclosed in U.S. Pat. Nos. 4,201,207; 4,318,400; 4,386,929 and 4,597,758.

Presumably, these patented devices provide portability of the infusion pump and provide a range of discrete value restrictors to assure a proper selection of infusate flow rates. In practice, however, the flow rate cannot be precisely selected to suit the needs of a particular patient. Flow rate of the infusate is dependent on a number of factors such as the bore size of the restrictor and the fluid properties of the infusate. The bulk viscosity, for example, varies from fluid to fluid and is further dependent on the infusate's dispensing temperature. Moreover, infusates containing suspensions often cannot pass through the restrictors because the suspension particles become lodged in the bores or clog the filter elements. Accordingly, a wide range of discrete value restrictors as well as an astute knowledge of the infusate fluid properties must be made available to provide the desired flow rate for a particular infusate. Due to the economics and logistics, however, only the most common discrete value restrictors are produced and made widely available.

Osmotic infusion devices based on the Rose-Nelson pump principle have been developed which are activated by imbibition of water (S. Rose and J. F. Nelson, "A Continuous Long-Term Injector", *Austral. J. exp Biol.* 33, pp. 415–420 (1955)). A Rose-Nelson pump consists of three chambers: a salt chamber containing excess solid salt, an infusate chamber and a water chamber. The salt and water compartments are separated by a rigid semipermeable membrane permeable to water but impermeable to salt; the salt and infusate chambers are separated by a elastomeric diaphragm. As water is imbibed osmotically into the salt chamber, the salt chamber swells causing the elastomeric diaphragm to expand into the infusate chamber which forces the infusate therefrom through a delivery orifice. Examples of these osmotic infusion devices may be found in U.S. Pat. Nos. 3,604,417; 3,760,984; 3,845,770; 4,193,398; 4,474,575, 4,474,048; 4,552,561; and 4,838,862. Generally, the flow rate of the infusate of these devices is controlled by osmotic rate controllers which vary one or a combination of the: osmotic gradient, a function of the salt; the area of the semipermeable membrane, as well as the membrane's property characteristics.

However, similar to non-osmotic portable and disposable infusion pumps including discrete value internal restrictors, a variety of osmotic rate controllers must be available to suit the particular parenteral treatment needs of the patient. Again, because of economics and logistics, only the most common flow rates are provided for and made widely available.

Another form of drug dispensing is that provided by electrochemically driven drug dispensers. Generally, a first compartment is provided containing electrochemically active fluid molecules (in gas form). Disposed adjacent to the first compartment is a second compartment which is separated therefrom by an electrolytic membrane. An electrode contained in the first compartment acts as a catalyst in converting the fluid molecules in the first compartment to ions so that passage through the electrolytic membrane is permitted. An opposing electrode contained in the second compartment reconverts or recombines those ions back to fluid molecules in the second compartment. The net result is that fluid from the first compartment is recombined in the second compartment to fill the second compartment. The recombined fluid molecules create fluid pressure on an expandable diaphragm separating the second compartment from a drug containing chamber. In turn, the expanding diaphragm expels the drug from the chamber. Hence, the fluid pressure is determined by the magnitude of an electric current applied between the two opposing electrodes in conductive contact with the membrane and the diffusion rate through the membrane. Typical examples of these true electrochemically driven infusion devices may be found in U.S. Pat. Nos. 4,687,423 and 4,886,514.

While these devices may provide adequate dispensing of a drug under certain circumstances, some problems are inherent with these designs. In order to electrochemically convert the fluid molecule in the first compartment to an ion and then reconvert that ion back to a fluid molecule on the other side of the electrolytic membrane, a constant current must be applied between the electrodes. Hence, a power source is always required to provide this sustained current for the duration of the dispensing period. Moreover, since the fluid employed to drive the diaphragm is generally gaseous, it is highly susceptible to external environmental changes, such as temperature. Accordingly, the pressure exerted on the diaphragm may vary in these instances and ultimately change the rate of dispensing the drug.

More recently, though still in its infancy, electrochemically controlled dispensing mechanisms for drug delivery have been developed. These infusion pumps, incorporating electrochemical mechanisms, generally include a layered composite of a microporous alumina membrane and a gold microporous electrode coated with an impermeable overlay barrier which spans and covers the micropores of the electrode. On one side of the composite is a dispensing reservoir of infusate in flow contact with the electrode and the barrier which prevents the infusate from flowing through the micropores and into a dispensing channel. Hence, by opening the barrier layer covering the electrode micropores, the infusate is permitted to pass through the layered composite and into the recipient via the dispensing channel (M. J. Tierney and C. R. Martin, "Electrorelease Systems Based on Microporous Membranes", *J. Electrochem. Soc.* Vol. 137, No. 12, pp. 3789–3793 (1990)).

To open this barrier layer, two general techniques are currently employed. The first and more refined technique involves disruption or dissolution of the barrier layer by passing a current through the overlayer. This dissolvable material layer, preferably a thin metal foil, is oxidized galvanostatically and dissolved into the infusate solution, thereby opening the micropores for flow of the infusate therethrough. The second technique employed to "open" the micropores generally involves an overlayer of a polymeric based barrier material which spans the micropores and is impermeable to the infusate. In general, a gas is generated by electrolysis of the infusate on the electrode behind the polymer membrane which ruptures the polymer membrane, thereby uncovering the micropores. Because the electrochemistry is carried out in the medicament or fluid, the infusate is contaminated. Unpredictable chemical reactions or electrochemical reactions could occur, resulting in toxic products which would be infused into the recipient. The dispensed drug, for example, could be undesirably modified. Moreover, since the infusate must flow through the micropores of the membrane, the flow rate cannot accurately be controlled without careful consideration of the infusate fluid properties (i.e., bulk viscosity), the size of the micropores, and the area of disruption.

None of the foregoing references is believed to disclose the present invention as claimed and is not presumed to be prior art. The references are offered for the purpose of background information.

SUMMARY OF THE INVENTION

Accordingly, it is an object of the present invention to provide a dispensing assembly and method for dispensing an infusate which can be delivered at a selective and controlled rate of infusion independent of the viscosity or nature of the suspension being infused.

It is another object of the present invention to provide a selective and controlled rate dispensing assembly and method for dispensing an infusate which is electrochemically controlled.

Another object of the present invention is to provide an infusion pump assembly and method for dispensing an infusate which separates the infusate from the contaminating electrochemistry.

Yet another object of the present invention is to provide an infusion pump assembly and method for dispensing an infusate which is portable, is complete with drug and pump driving fluid, and can be stored for prolonged periods without deterioration.

It is another object of the present invention to provide a selective and controlled rate infusion pump assembly and method for dispensing an infusate which can be activated quickly and simply.

Still another object of the present invention is to provide an infusion pump assembly and method for dispensing an infusate which automatically adjusts to maintain a steady flow rate.

It is a further object of the present invention to provide a selective and controlled rate infusion pump assembly and method for dispensing an infusate which is durable, compact, easy to maintain, has a minimum number of components, is easy to use by unskilled personnel, and is economical to manufacture.

It is a still further object of the invention to permit a user to deliver a pulse of an infusate when needed or desired. This enables, for example, patients with certain medical conditions, such as pain associated with bone cancer (PCA—patient controlled analgesia) or pre-term labor control (Terbutylene therapy) to have a steady background delivery rate and periods of short pulses or boluses of medication to achieve the desired therapeutic effect.

The present invention includes an infusion pump assembly for controlled infusion of a dispensing fluid. A partition is provided having a front surface and an opposite facing back surface, and defines an aperture extending from the front surface to the back surface. On one side of the partition is a driving fluid reservoir formed for storing a driving fluid therein which is in communication with the aperture for flow of the driving fluid through the partition. A plug member is disposed in the aperture in a manner preventing flow of the driving fluid through the partition. The infusion pump further includes an electric control device operably and temporarily coupled to the plug member for controlling passage of the driving fluid through the aperture. A barrier defines a receiving reservoir and is positioned relative to the aperture for receipt and containment of the driving fluid in the receiving reservoir as the driving fluid flows from the driving fluid reservoir through the aperture. The barrier is formed to expand from a first volume toward an increased second volume in response to receipt of the driving fluid in the receiving reservoir. A dispensing reservoir is provided for holding the dispensing fluid therein and includes an orifice for release of the dispensing fluid therethrough. The barrier separates the dispensing fluid from the driving fluid, and further is mounted for movement into the dispensing reservoir to communicate with the dispensing fluid to urge the dispensing fluid through the orifice as the barrier moves toward the increased second volume. A driving force is coupled to the driving fluid reservoir for urging the driving fluid through the aperture into the receiving reservoir when the electric control device permits passage of the driving fluid therethrough. The flow of the dispensing fluid can be temporarily increased, such as by using a one-way pulse pump to deliver a pulse of driving fluid directly into the receiving reservoir.

In another aspect of the present invention, a method of controlled infusion of an infusate is provided comprising the step of: activating the electronic control device to effect the opening of the plug member for controlling passage of the driving fluid from the driving reservoir through the aperture and into the receiving reservoir. Upon receipt of the driving fluid in the receiving reservoir, the barrier member expands from a first volume toward an increased second volume causing the dispensing fluid to release through the orifice in the dispensing reservoir.

Accordingly, the present invention provides a disposable electrochemical controlled dispensing assembly having a selectable and controllable infusion rate.

The invention is especially suited for medical uses. However, the invention can be applied to other activities where fluids are to be delivered at near uniform rates over, for example, days or weeks. For example, the invention can be used to aid delivery of air fresheners, fertilizers for home plants, sterilants or sanitizers.

BRIEF DESCRIPTION OF THE DRAWINGS

The assembly of the present invention has other objects and features of advantage which will be more readily apparent from the following description of the Best Mode of Carrying Out the Invention and the appended claims, when taken in conjunction with the accompanying drawing, in which:

DESCRIPTION OF THE PREFERRED EMBODIMENTS

Figure 1A:
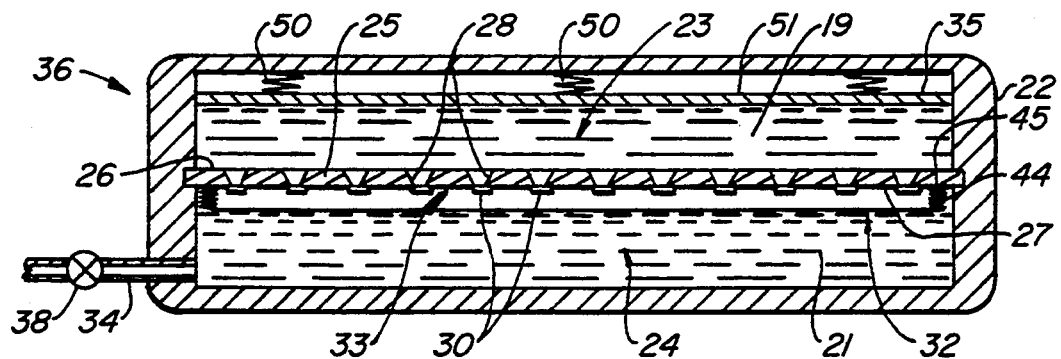
FIG. 1A is a front elevation view, in cross-section and partially diagrammatic, of a disposable electrochemically driven infusion pump assembly constructed in accordance with the present invention illustrating a separating bellows-type barrier in a collapsed condition.

The following description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded with the widest scope consistent with the principles and features disclosed herein. It will be noted here that for a better understanding, like components are designated by like reference numerals throughout the various figures.

Figure 1B:
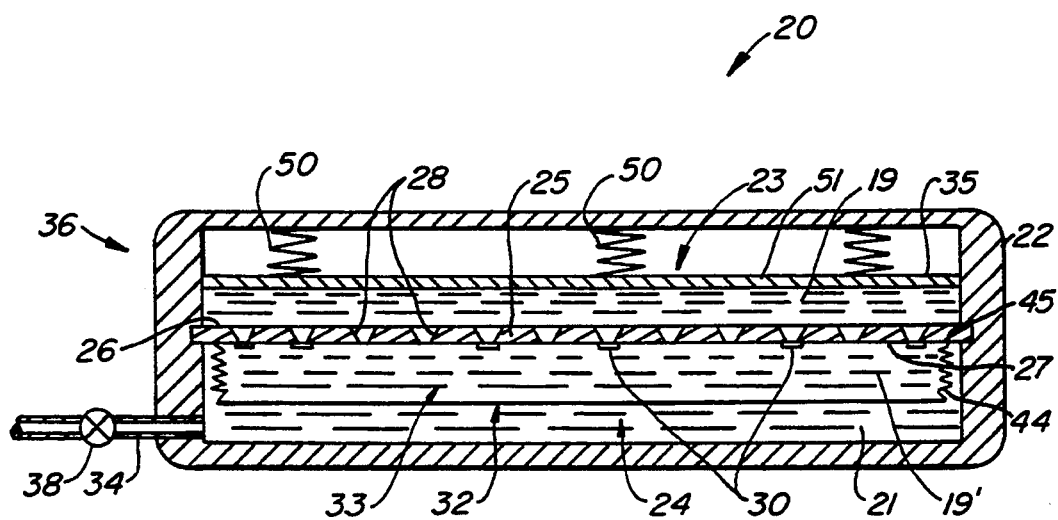
FIG. 1B is a front elevation view, in cross-section and partially diagrammatic, of the disposable infusion pump assembly of FIG. 1A illustrating movement of the separating barrier toward an increased or expanded condition to expel an infusate from a dispensing chamber.

Attention is now directed to FIG. 1, where the subject disposable infusion pump assembly, generally designated 20, for selective and controlled infusion of a dispensing fluid (infusate) 21 is illustrated. Briefly, the present invention includes a rigid housing or enclosure member 22 providing an internal cavity. A partition member, generally designated 25, extending transverse to a cross-sectional dimension of the internal cavity, divides the cavity into a driving reservoir 23 on one side (front surface) 26 of the partition and a dispensing reservoir 24 on an opposite side (back surface) 27 of the partition. Partition 25 provides at least one aperture 28 extending from front surface 26 to back surface 27. The driving reservoir or chamber is preferably positioned on the front surface side of partition 25 and is formed for storing a driving fluid 19 which is in communication with aperture 28 for flow of the driving fluid through partition 25. A plug member 30 is disposed in aperture 28 in a manner preventing flow of driving fluid 19 through the partition. The infusion pump further includes electric control means 31 (FIG. 2) operably and temporarily coupled to plug member 30 for controlling passage of driving fluid 19 through aperture 28. A barrier means, generally designated 32, defines a receiving reservoir 33 and is positioned in dispensing reservoir or chamber 24 relative to aperture 28 for receipt and containment of received driving fluid 19' in the receiving reservoir as the driving fluid flows from the driving reservoir through aperture 28. The barrier is formed to expand from a first volume (FIG. 1A) toward an increased second volume (FIG. 1B) in response to receipt of driving fluid 19' in receiving reservoir 33. The dispensing reservoir contains the dispensing fluid therein and includes an orifice 34 for release of the dispensing fluid therethrough. Barrier means 32 separates dispensing fluid 21 from the driving fluid, and further is mounted for movement into dispensing reservoir 24 to communicate with dispensing fluid 21 to urge the dispensing fluid through orifice 34 as barrier means 32 moves toward the increased second volume. A driving force means, generally designated 35, communicates with driving reservoir 23 for urging driving fluid 19 through aperture 28 into receiving reservoir 33 when electric control means 31 permits passage of driving fluid 19 therethrough.

In accordance with the present invention, a disposable infusion pump assembly 20 is provided which employs electrochemistry to selectively control the delivery rate of infusate (dispensing fluid) 21 from dispensing reservoir 24 by selectively controlling the flow rate of the driving fluid from the driving reservoir to the receiving reservoir. As will be described in greater detail below, infusion pump assembly 20 includes a disposable infusion pump unit 36 and a separate and remote programming unit 37 (FIG. 2) which forms a portion of electronic control means 31. Initially, once the proper dosage regimen has been prescribed, the separate and remote electronic programming unit can be calibrated to administer the proper infusate flow rate by selectively controlling the corresponding flow rate of driving fluid 19. This is accomplished first by temporarily electrically connecting programming unit 37 and disposable pump unit 36 together through a port connector 40. This permits electronic communication between programming unit 37 and plug member 30 to control passage of driving fluid 19 through aperture 28. Subsequently, programming unit 37 can be disconnected from disposable infusion pump unit 36, which acts independently as a medicament infusion pump at the proper selected fixed infusion rate. In one embodiment, after the flow rate has been activated, the present invention only operates as a fixed rate flow infusion pump and can only be turned on or off using valve means 38. In an alternative embodiment, as will be discussed in greater detail below, the disposable unit may actively change the delivery rate of the disposable pumping unit.

The present invention offers several advantages over the prior experimental electrochemically driven infusion devices and portable infusion pumps. By effectively employing electrochemistry to control the passage of driving fluid through aperture 28, the infusate rate can be selectively controlled with a precision unobtainable in the prior disposable infusion pumps. Hence, as will be further detailed below, the disposable infusion pump of the present invention is capable of providing a wide range of infusate flow rates without requiring multiple or combination of multiple parts. Further, barrier means 32 separates the electrochemistry in the driving fluid from the infusate so that cross contamination is eliminated. Moreover, by providing a separate and remote programming unit, the infusate flow rate can be initially set by a physician, medical technician or the like. Patient error and/or abuse in the operation of the infusion pump, therefore, is substantially reduced. Just as importantly, the more costly electronic components of electronic control means 31 can be incorporated with programming unit 37 and need not be disposed of when disposable pump unit 36 is no longer needed. The present invention, further, does not require that a constant current be applied to plug member 30 so as to permit passage of driving fluid 19 therethrough. Accordingly, it is not necessary for disposable pump unit 36 to include an independent power source. Finally, because barrier means 32 separates the driving fluid from the dispensing fluid, a wider range of possible electrochemistries can be utilized as compared to the experimental models where the electrochemistry was carried out directly in the infusate.

In the preferred embodiment of the present invention and as shown in FIG. 1A-2 and 5-6, partition 25 provides a plurality or an array of individual apertures 28 each including a plug member 30 which prevents driving fluid 19 from passage therethrough into receiving reservoir 33. As best viewed in FIG. 2, electronic control means 31 provides that each plug member 30 is individually addressable through electrical leads 41 (FIG. 2) to independently control passage of driving fluid 19 through respective apertures 28. Thus, by knowing the fixed geometry of the aperture, the viscosity of the driving fluid and the driving pressure urging the driving fluid through the aperture, an accurate calculation of the driving fluid flow rate through the individual aperture can be determined. Accordingly, by activating the passage of driving fluid through a discrete and predetermined combination of apertures, the collective flow rate of the driving fluid can be precisely controlled which, in turn, precisely expels the infusate at a controlled flow rate from dispensing reservoir 24 through dispensing orifice 34. As viewed in FIG. 2, apertures 28 can be of differing shapes and sizes or may all be similarly formed (i.e., FIG. 1). Regardless, programming unit 37 will be preprogrammed or calibrated, as a function of the driving fluid viscosity and driving force, to operate a predetermined combination of apertures for selective and controlled flow rate of driving fluid 19. It will be appreciated, however, that any number and/or combination of apertures may be provided without departing from the true spirit and nature of the present invention.

Briefly, infusate 21 is preferably a liquid based "drug" or "medicament" solution which denotes any medication composition; in any way affecting any human or animal entity; substance to be assimilated by any human being or animal for its nourishment or for regulating its growth; and substance having any other effect on any other environment, especially any aqueous environment. Infusate 21 can also be any other fluid which is to be delivered in a controlled manner, to include fluids used with air freshness, fertilizers for house plants, sterilants and sanitizers. Thus, pump assembly 20 can be used in both medical and non-medical applications.

Protective enclosure 22 is preferably a rigid housing constructed of materials that are relatively impervious to invasion by environmental agents such as oxygen, carbon dioxide, or substances that are derived from components of the device. The internal cavity dimensions of enclosure 22 will vary according to the desired volume of the driving reservoir and the dispensing reservoir.

Partition 25 fixedly mounts transversely to the internal cavity and prevents fluid communication between driving reservoir 23 and dispensing reservoir 24, except through apertures 28. In the preferred form, partition 25 is provided by a silicon plate member. The array of precision sized apertures or pores 28 are fabricated using silicon micromachining techniques known in the field. As viewed in FIGS. 2 and 3, apertures 28 are preferably obelisk-shaped having side walls inclined from a horizontal of approximately 54.7°. Such precision may be fabricated using further known techniques of anisotropic etching.

Figure 3:
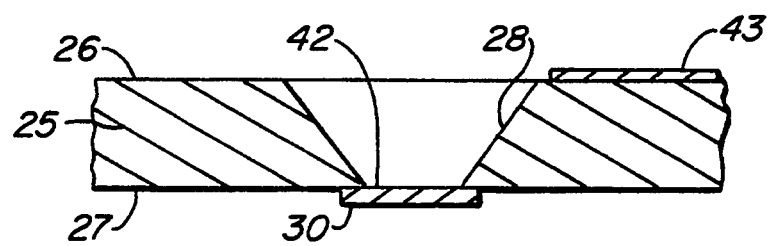
FIG. 3 is an enlarged, fragmentary front elevation view, in cross-section, of an individual aperture of the disposable infusion pump assembly of FIG. 1A employing a dissolvable plug member.

As previously stated, passage of driving fluid 19 through unblocked apertures 28 is permitted employing electrochemical techniques similar to those described in the M. J. Tierney and C. R. Martin article mentioned above to unblock apertures. In the preferred form, individual plug members 30 are to be formed of an electroerodible, or dissolvable type material such as an easily-oxidizable metal film. FIG. 3 best illustrates that the metal film, such as silver, could be disposed in or grown across aperture 28 in a manner preventing passage of driving fluid 19 therethrough. Preferably, individual metal film plugs are grown across the aperture proximate back surface 27 by deposition (e.g., electroplating) onto a sacrificial layer (not shown) which is subsequently removed.

Each metal film plug 30 includes a driving fluid facing surface 42 in flow contact with driving fluid 19, and each is connected to an individual electrical lead 41 (FIG. 2) in a commonly known manner. When leads 41 are temporarily and operably coupled to remote programming unit 37 (via port connector 40), each metal film plug 30 essentially forms an individually addressable electrode in flow contact with driving fluid 19. Thus, by providing a large counter electrode 43 or multiple counter electrodes 43 separate and apart from film plug/electrode 30 and in flow contact with driving fluid 19, individual electrical circuits can be formed when the driving fluid is an electrolyte. As best viewed in FIG. 3, counter electrode 43 is preferably disposed on front surface 26 of partition 25 proximate each aperture 28.

When a current, having a sufficient current density, is applied between a selected metal film plug/electrode 30 and the corresponding counter electrode 43, the metal film plug/electrode 30 is caused to be quickly and efficiently galvanostatically oxidized or dissolved into solution. Aperture 28 will then be discretely unblocked (irreversibly) for controlled passage of driving fluid therethrough. Accordingly, depending on the driving fluid viscosity and the driving force acting on the driving fluid, programming unit 37 can be calibrated to individually address one or any combination of electrical circuits to oxidize desired metal plug/electrodes 30 and produce the desired driving fluid flow rate.

It will be appreciated that due to the uniform thinness of metal film plug/electrode 30, the plug is quickly and completely dissolved so that aperture 28 is discretely opened for precision flow control therethrough. Blockage, therefore, of aperture 28 by a partially eroded plug will not occur. It will further be understood that the current applied to electrode 30 by programming unit 37 need only be initially applied to dissolve the film plug. Portability of dispensing unit 36, hence, is enhanced since the unit need not carry an independent power source to permit passage of driving fluid 19 through selected apertures 28. It will also be apparent that an Ohm's Law relation can be used to validate the complete opening of the apertures Referring back to FIG. 1A, initially, all apertures are blocked via plug members 30. Once plug member 30 or combination of plug members 30 has been dissolved or opened (FIG. 1B), driving fluid 19 (via driving force means 35 discussed below) begins to flow from driving reservoir 23 through unblocked aperture 28 for receipt in receiving reservoir 33. Barrier means 32, positioned proximate back surface 27 of partition 25, is of a material impermeable to both driving fluid 19 and infusate 21. Further, the barrier sufficiently surrounds all apertures at back surface 27 so that all driving fluid 19' passing through the unblocked apertures is received in receiving reservoir 33 and is completely isolated from infusate 21.

Accordingly, as driving fluid 19 is deposited in receiving reservoir 33, the volume of received driving fluid moves from a first volume (FIG. 1A) toward an increased second volume (FIG. 1B). As best viewed in FIGS. 1A and 1B, such volume increase positively displaces barrier means 32 into dispensing reservoir 24 which expels infusate 21 therefrom through dispensing orifice 34 at a preferable one-to-one ratio. The fixed rate of flow of driving fluid 19 through apertures 28 expands the volume of barrier 32 toward increased second volume at a constant rate to assure precision dispensing of infusate 21.

Briefly, dispensing orifice 34 is formed and dimensioned to receive a standard skin-piercing needle or drug delivery set for intravenous use. Alternatively, orifice 34 may receive an apparatus formed to be inserted into one of the normal body orifices. Orifice 34, when not used in a medical setting, can be formed and dimensioned according to the particular end use contemplated.

In one preferred embodiment, separating barrier 32 is provided by an expandable bellows-type barrier (FIG. 1A and 1B) 32 which includes pleated walls 44 formed to positively displace into dispensing reservoir 24. Therefore, bellow-type barrier 32 must be formed and dimensioned to expand into dispensing reservoir 24 without interference. An upper peripheral edge portion 45 is formed to completely surround apertures 28, and to mount to and cooperate with back surface 27 of partition 25 to seal and isolate received driving fluid from dispensing fluid 21.

Figure 5:
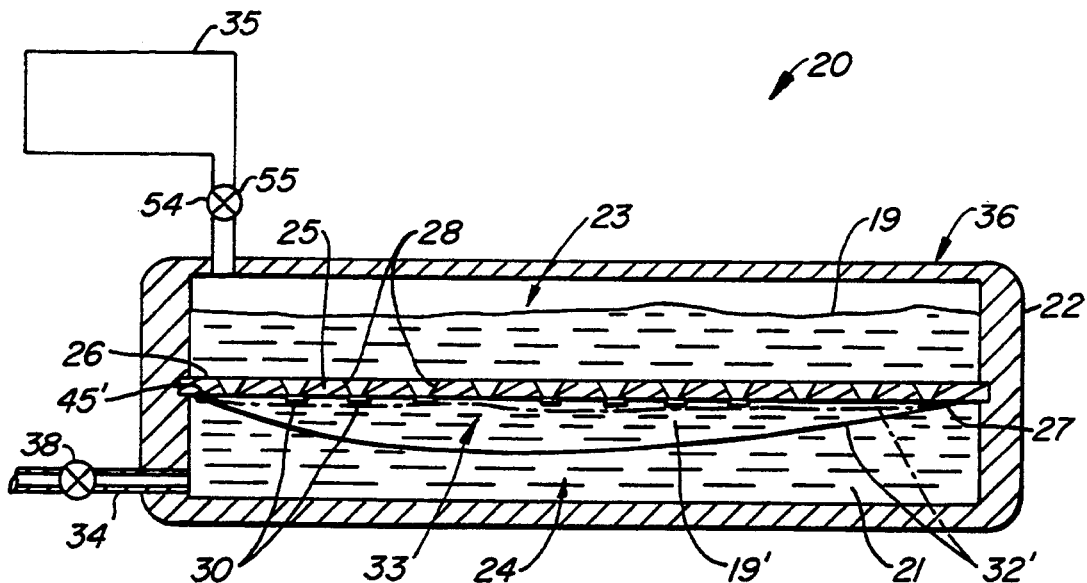
FIG. 5 is a front elevation view, in cross-section and partially diagrammatic, of an alternative embodiment of the disposable infusion pump assembly of FIG. 1A and employing an elastomeric diaphragm as a separating barrier.

Alternatively, as viewed in FIG. 5, the barrier means may be provided by an elastomeric diaphragm 32' having a peripheral edge portion 45' which is also dimensioned to completely surround apertures 28, and to mount to and cooperate with back surface 27 of partition 25 to seal and isolate received driving fluid 19' from dispensing fluid 21. Elastomeric diaphragm barrier 32' is further formed to swell or stretch upon receipt of driving fluid 19' in receiving reservoir 33 from the first volume (defined in phantom lines as collapsed diaphragm barrier 32') toward the increased second volume (defined in solid lines as expanded diaphragm barrier 32'). Again, receipt of driving fluid expands and moves barrier 32' into dispensing reservoir 24 which positively displaces and expels infusate 21 therefrom.

Figure 6:
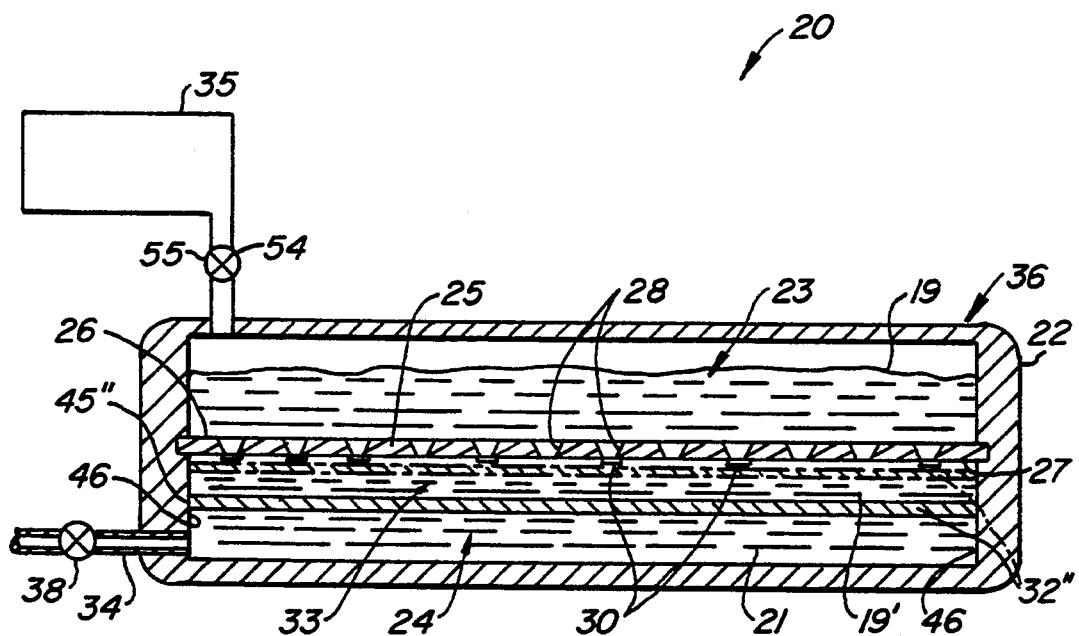
FIG. 6 is a front elevation view, in cross-section and partially diagrammatic, of an alternative embodiment of the disposable infusion pump assembly of FIG. 1A and incorporating a movable wall as a separating barrier.

A third embodiment of the barrier, illustrated in FIG. 6, is provided by a movable barrier partition 32'' or piston member which expels the infusate from dispensing reservoir as receiving reservoir 33 expands from the first volume (defined by barrier 32'' in phantom lines) toward increased second volume (defined by barrier 32'' in solid lines). It will be appreciated that the movable barrier partition is preferably substantially rigid and includes an outer perimeter edge portion 45'' formed and dimensioned to slidably cooperate and seal against inner side walls 46 forming dispensing reservoir 24. Accordingly, inner side walls 46 are preferably substantially perpendicular to back surface 27 of partition 25 so that movable barrier partition 32'' can slidably cooperate and seal therewith.

It is desirable to utilize driving fluids having the same or similar fluid viscosity which substantially simplifies flow rate calibrations. Moreover, because the same driving fluid medium is flowing through the apertures in all instances, the infusate delivery rate will be independent of the infusate viscosity which is a problem with most prior art infusion pumps. In the preferred form, isotonic saline solution is provided as the driving fluid. A saline solution is desirable because of its efficient electrochemical properties as well as its safeness in use should the barrier rupture or a leak occur.

As above-mentioned, driving force means or mechanism 35 is communicably coupled to driving reservoir 23 for urging driving fluid 19 through selected apertures 28 and into receiving reservoir 33. The pressure exerted on driving fluid 19 by driving force mechanism 35 constitutes one of the factors necessary to accurately determine the driving fluid flow rate. Therefore, it is preferable to maintain a uniform pressure on driving fluid 19 so that fluid flow is substantially constant.

Driving force mechanism 35 may be provided by a variety of pressure generating mechanisms commonly used in other portable infusion pump assemblies. Preferably, these mechanisms provide a driving force between 15–20 psi. Such forms of energy include, but are not limited to: temperature controlled vapor pressure to control pressure; electrolysis of a solution to produce a gas exerting a pressure on the driving fluid; compressed gases; storage of a fluid under pressure in an elastomeric compartment; capillary forces; osmotic pressure caused by the expansion of a volume as fluid permeates through a semipermeable membrane into a salt chamber; and mechanical power sources, such as a compression spring element acting on a movable piston in pressure communication with the driving fluid. Several of these driving force mechanisms are discussed in greater detail in U.S. Pat. No. 5,135,498.

In the preferred form and as best viewed in FIGS. 1A and 1B, driving force mechanism 35 is provided by a constant mechanical driving force 50 acting against a movable platform or piston member 51 which causes the platform to exert a constant pressure on driving fluid 19. Once platform 51 moves into driving reservoir 23 and against driving fluid 19, the driving fluid is positively displaced from the driving reservoir through the selected apertures 28 (FIG. 1B). Most preferably, the mechanical driving force is provided by a plurality of spaced-apart compression spring members 50 which generate a balanced low intensity and constant force against platform 51, biasing it into positive pressure contact with the driving fluid.

Driving force mechanism 35 may also be provided by expansion of a gas generating a driving pressure on driving fluid 19. As shown in FIGS. 5 and 6, this may be performed by pressurizing driving reservoir 23. This form of driving energy is simple to construct and easy to maintain. A pressure valve or the like (not shown) may be provided so that the pressure can be maintained and/or changed.

In still another alternative embodiment of the present invention, plug members 30 may be comprised of a switchable gate membrane 30 capable of opening, permitting driving fluid 19 to pass through selected apertures 28, and closing, preventing passage of fluid 19 through apertures 28. Unlike the above-mentioned electro-erodible or dissolvable plug members, switchable gate membranes can be selectably and reversibly opened and closed in a manner analogous to a microvalve. This reversible capability, hence, not only initiates dispensing of the drug (dispensing fluid 21), but also may stop or reduce flow of the drug. Accordingly, these individually addressable gate elements provide precise control of the driving fluid for both a constant or variable rate of flow. As will be described in greater detail, by opening and/or closing selected gate membranes 30 at precalculated or preprogrammed times or intervals, complex drug treatment regimens can be administered for optimum drug efficacy.

Figure 4:
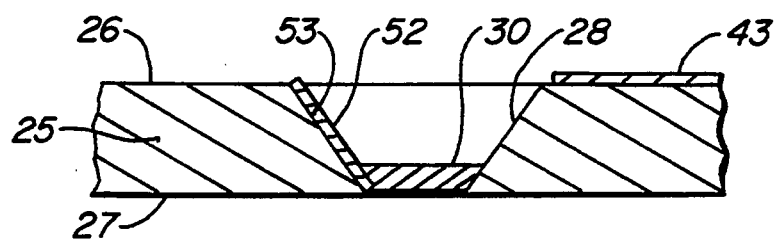
FIG. 4 is an enlarged, fragmentary front elevation view, in cross-section, of an individual aperture of the disposable infusion pump assembly of FIG. 1A employing a switchable gate plug member.

FIG. 4 illustrates an individual switchable gate membrane 30 disposed transversely across aperture 28 in a manner preventing flow of driving fluid 19 therethrough. An individual plug electrode 52 (contrary to the dissolvable plug members 30 where the plug was the electrode) is preferably positioned against a side wall 53 of aperture 28 and in conductive contact with gate membrane 30 and (although not necessarily) driving fluid 19. Gate membrane 30, therefore, can be individually switched between the opened condition and the closed condition through programming unit 37 via contact with plug electrode 52.

In the preferred embodiment, switchable gate membrane 30 is provided by an electrochemically active polymer membrane having a natural or manufactured porosity sufficient to permit whole molecules of aqueous driving fluid to flow through the membrane. As will be described in more detail below, these electroactive polymers are capable of repelling the molecules of aqueous liquid so that they are unable to pass through the pores. Through electrochemistry initiated by programming unit 37 and plug electrode 52, gate membrane 30 can be selectively changed between a polar (hydrophilic) condition, permeable to driving fluid 19 (preferably an aqueous electrolyte), and a non-polar (hydrophobic) condition, impermeable to the driving fluid. More specifically, the gate membrane polymers are composed of a material such as Nafion ® which is switchable between a hydrophilic condition (permeable to water or saline) and a hydrophobic condition (impermeable to water or saline). By modulating the hydrophilicity of individually addressable polymer gate membranes, the flow rate of the driving fluid (water) from driving fluid reservoir 23 to receiving reservoir 33 can be constantly or variably controlled.

Because barrier member 32 separates and isolates the electrochemistry contained in the driving fluid from the dispensing fluid, as stated, the same gate membrane and the same driving fluid may be employed in most instances to dispense the drug from dispensing reservoir 24. This eliminates the need for tailoring the polymer membrane to the chemical characteristics of the specific medicament or drug to be dispensed.

According to Mark W. Espenscheid et al., "Sensors from Polymer Modified Electrodes", *J. Chem. Soc., Faraday Trans.* 1, 82, 1051 (1986), polymer membrane 30 may comprise a manufactured or naturally porous film capable of passing intact water molecules therethrough. Preferred membranes include ionomer films, such as Nafion ®. An ionomer is a near or branched organic polymer which contains low concentrations of ionizable groups and which is not covalently cross-linked. Nafion ® has been shown to possess a preference for incorporation of large, electroactive hydrophobic cations, such as methyl viologen or a variety of transition metal complex cations, such as $Ru(NH_3)_6^{3+}$, $Ru(bipy)_3^{3+}$, where bipy=3,2'-dipyridine, and ferrocenylmethyltrimethylammonium, upon electrochemical treatment. Hence, upon selective ion exchange and the resulting incorporation of a given hydrophobic cation, these ionomer membranes can be modified to repel or reject passage of water therethrough, thereby preventing the passage of aqueous driving fluid molecules through the pores of the membrane. In an alternate embodiment, an ionically conductive composite polymer membrane may be utilized, such as Nafion ® impregnated Gore-tex.

Alternatively, electroactive ionomers containing both electroactive and ion-exchange functionalities, such as terpolymers based upon styrene, vinylferrocene and styrene sulphonate, may be used. These polymers have been shown to reversibly electrorelease incorporated hydrophobic counterions. More particularly, when the electroactive functionality in the terpolymer (in this case, vinylferrocene) is in the reduced state, the ion-exchange functionality (styrene sulphonate) requires a counterion, thereby promoting incorporation of hydrophobic cations from the surrounding electrolyte solution and altering the electrochemical characteristics of the film so that the resultant modified polymer film repels water. Hence, when a counterion, for example, $Ru(bipy)_3^{3+}$, is incorporated into the ionomer film, the polymer membrane becomes much more hydrophobic (water impermeable) in nature so that the driving fluid cannot flow through the membrane.

Through contact with electrode 52 and upon exposure to an electrolyte solution (i.e., in driving fluid 19), the electroactive functionality in the ionomer can be oxidized, resulting in an electrorelease or expulsion of the hydrophobic counterion from the film and into the solution. Once the counterion is expelled, the electrochemical characteristic of the polymer membrane is reversibly changed to a hydrophilic state and the water molecules are permitted to pass through the pores of the membrane. By knowing the flow characteristics of the polymer membrane, the surface area of the aperture and the driving force, the flow rate of the driving fluid therethrough can be calculated and controlled.

Moreover, by reversing the polarity of the polymer membrane (via electrode 52), the ionomer film (polymer membrane) can be electrochemically reduced so that the counterions are drawn from the solution and reincorporated back into the polymer membrane. Accordingly, by reversing the polarity of the membrane, the hydrophilicity of the polymer can be modulated in a controlled manner and the apertures can be opened and closed through programming unit 37.

Again, it will be appreciated that the current applied to electrode 52 by programming unit 37 to set the polarity of membrane 30 need only be initially applied. Should the flow rate of the driving fluid need to be changed subsequently for more complex drug regimens, as will be described below, only a limited duration current is necessary to reverse the polarity of the membrane.

One type of electrochemically active gate polymers are the conductive polymers which can be selectively electrochemically switched between an electrically conducting state (hydrophilic or water-permeable) and an electrically insulating state (hydrophobic or water-impermeable). In the conducting state, gate polymer 30 is generally oxidized and contains positively charged sites on the polymer chain which increase its hydrophilicity. When switched to the insulating state, the hydrophilicity decreases, and the polymer is no longer water-permeable.

Another type of electrochemically active gate polymers are the electroactive polymers which include side groups that can be electrochemically oxidized and reduced. Similar to conductive polymers, in an oxidized state, the gate polymer generally contains positively charged sites on the polymer chain which increase its hydrophilicity. When switched to the reduced state, the hydrophilicity decreases, and the polymer is no longer water-permeable.

Once disposable dispensing unit 36 has been temporarily electrically coupled to programming unit 37 (via connector 40) the dosage regimen can be initially set by operating programming unit 37. Depending on the corresponding flow rate, programming unit 37 will automatically select a particular one or predetermined combination of plug members 30 to oxidize or dissolve into the driving fluid solution (taking into consideration the driving pressure and driving fluid viscosity) discretely opening the corresponding aperture.

Driving force mechanism 35 may include an activation device 54, as shown in FIGS. 5 and 6, which permits the pressure exerted by the driving force mechanism to act on driving fluid 19 contained in the driving reservoir. Device 54 may be provided by a simple manually operable valve or may include an electronic switch. Similarly, as a further precaution, drug delivery may begin or be stopped upon opening or closing manual valve 38 at orifice 34.

When the flow rate has been programmed and activated, the disposable pump unit can be disconnected from programming unit 37. In one embodiment of the present invention, pump unit 36 operates only as a fixed rate unit and can only be turned on or off using manual valve 38. A second microprocessor (not shown), incorporated in disposable unit 36, may be coupled to driving mechanism 35 which is capable of micro-adjustments to maintain a more constant driving force.

In other embodiments, the dosage regimen may be varied by changing the driving fluid flow rate. To simply increase the flow rate, the disposable pump unit may be temporarily reconnected to the programming unit where additional apertures may be unblocked. More complex applications may include varying the force exerted on the driving fluid from the driving force mechanism. Driving force means 35, for example, may include pressure adjusting means 55 which controls the pressure exerted on driving fluid 19. Pressure adjusting means 55, may be provided by a pressure intake/exhaust valve or a valve capable of flow control. For a more detailed description of various pressure adjusting mechanisms, Athayde et al., U.S. patent application Ser. No. 07/503,719, is hereby incorporated by reference.

Furthermore, when employing switchable gate membranes 30, as stated above, selected gate membranes 30 may be opened and/or closed at precalculated or preprogrammed times or intervals so that complex drug treatment regimens can be administered for optimum drug efficacy. For example, disposable unit 36 may include a regimen microprocessor which is programmed (via programming unit 37) when disposable unit 36 is initially coupled to programming unit 37. The regimen microprocessor may store a set of commands which activate certain combinations of gate membranes 30 at predetermined times or intervals for flow rate control of the driving fluid. Moreover, since only a limited duration current is necessary to reverse the polarity of the membrane, only a very small power source needs to be incorporated in disposable unit 36. Accordingly, this embodiment permits more complex and precisely administered regimens from a portable dispensing unit.

Another embodiment of the present invention employing switchable gate membranes may include patient activated boluses, as used in pain management, where the patient may self administer the drug. In this embodiment, a manually operable switch electrically coupled to the regiment microprocessor may be self activated to administer precalculated (i.e., through programming unit 37) or limited quantities of drug within a predetermined time span.

Figure 2:
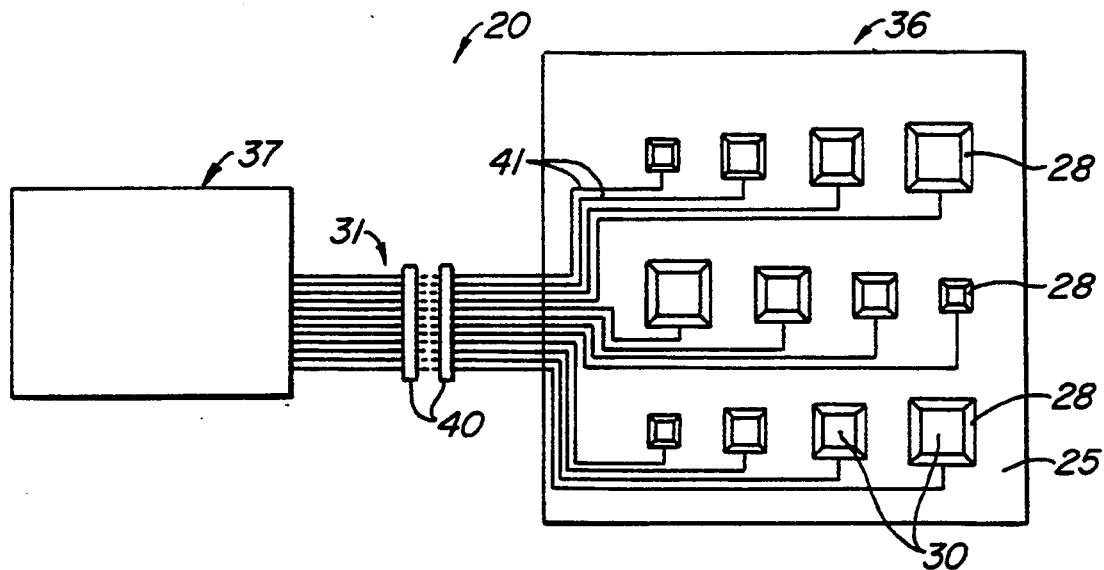
FIG. 2 is a schematic diagram of one embodiment of the present invention showing different sized apertures, provided in a partition member, each individually connected to a programming device.
Figure 7:
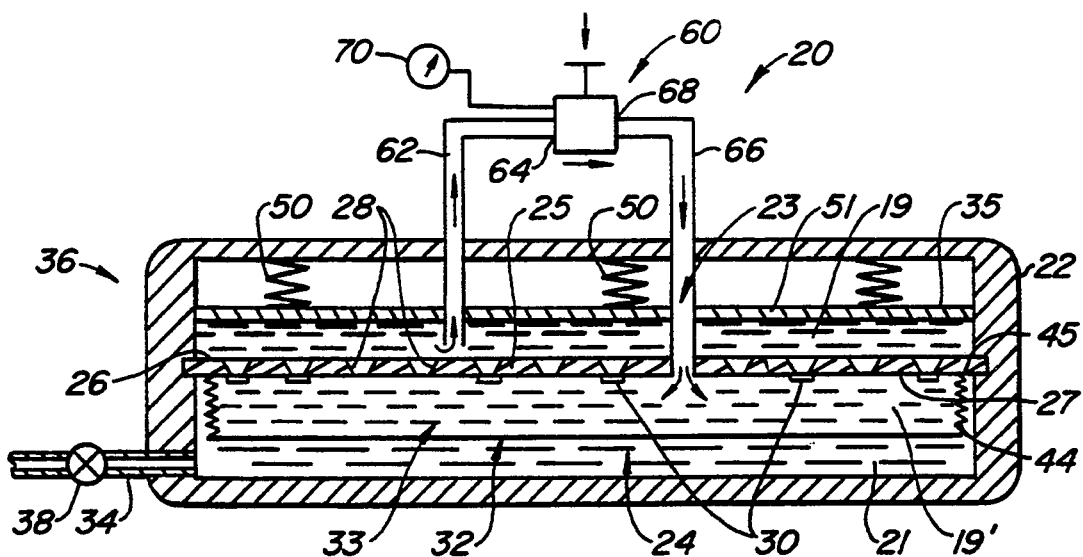
FIG. 7 is a view similar to that of FIG. 1B showing the use of a one-way pulse pump to provide a pulse or bolus of the infusate.

FIG. 7 illustrates a further alternative embodiment of the invention, similar to the embodiment of FIGS. 1-3, but modified to permit a different form of patient-activated, or other user-activated pulses or boluses of infusate 21. Pump unit 36 includes a one-way, user-activated pulse pump 60 coupled to an intake line 62 at its inlet 64 and an outlet line 66 at its outlet 68. Intake line 62 passes through platform 51 and opens into driving reservoir 23. Outlet line 66 passes through platform 51 and partition 25 and opens into receiving reservoir 33. Actuating pump 60 causes a pulse or bolus of driving fluid 19 to pass through line 62, pump 60, line 66 and into reservoir 33. This causes a corresponding pulse or bolus of infusate to be delivered through orifice 34 to, for example, a patient. To prevent over medication, actuation of pump 60 can be limited or controlled by a pulse frequency limiter 70 which acts to lock out pump 60 for, typically, a pre-set time period after pump 60 has been actuated. Pump 60 could be mechanically or electrically actuated. Intake line 62 could be coupled to a separate reservoir of driving fluid 19 instead of driving reservoir 23.

The disposable infusion pump unit of the present invention can be attached to the body of the wearer by means of a biocompatible adhesive coating on the base of the assembly, or by adhesive strips or overlays, and does not mandate the use of straps, belts, or other carrying garments. The device may be attached anywhere on the body that is convenient, either immediately adjacent to the delivery site, or at a point from that site.

Particularly when describing the source of the driving force of this invention, embodiments will employ components that are dependent on the resistance forces of the pump, the driving fluid employed, the infusate being delivered, and other variables. The choice of components used in the various foregoing general descriptions and the following detailed descriptions are exemplary and explanatory, but are not restrictive of the invention.

Because the devices described in the present invention are small and simple, they are particularly suitable for delivering small infusate volumes. The disposable pump unit of this invention, while it can be tailored for a range of infusate volumes and dosage rates, is particularly useful where the total infusate volume to be dispensed is of the order of one to 50 milliliters, and the delivery time for that volume is one hour to seven days. Thus, the invention enables therapy involving highly potent substances, such as peptide drugs of various kinds, heparin and insulin, analgesics and anesthetics, corticosteroids, immunosuppressants, antineoplastics, antibacterials, and antidotes to chemical or biological poisons and the like, to be administered without subjecting the patient to repeated injections or requiring the patient to be attached to an intravenous drip.

In another aspect of the present invention, a method of controlled infusion of an infusate is provided comprising the step of: activating electronic control device 31 to effect the opening of plug member 28 for controlling passage of driving fluid 19 from driving reservoir 23 through aperture 28 and into receiving reservoir 33. Upon receipt of the driving fluid in the receiving reservoir, barrier member 32 expands from a first volume toward an increased second volume causing dispensing fluid 21 to release through orifice 34 in the dispensing reservoir.

Other modifications and variations can be made to the disclosed embodiments without departing from the subject of the invention as defined by the following claims.

What is claimed is:

1. A pump assembly for controlled delivery of a dispensing fluid comprising:
   a partition having a front surface and an opposite facing back surface, and defining an aperture extending from said front surface to said back surface;
   a driving reservoir formed for storing a driving fluid therein and in communication with said aperture for flow of said driving fluid through said partition;
   plug means disposed in said aperture in a manner preventing flow of said driving fluid through said partition;
   electric control means operably coupled to said plug means for controlling passage of said driving fluid through said aperture;
   barrier means defining a receiving reservoir and positioned relative to said aperture for receipt and containment of said driving fluid in said receiving reservoir as said driving fluid flows from said driving reservoir through said aperture, said barrier means separating said dispensing fluid and said driving fluid, and further formed to expand from a first volume toward an increased second volume in response to receipt of said driving fluid in said receiving reservoir;

a dispensing reservoir for holding said dispensing fluid therein, said dispensing reservoir defining an orifice for release of said dispensing fluid therethrough, said barrier means being mounted for movement in said dispensing reservoir in a manner communicating with said dispensing fluid to urge said dispensing fluid through said orifice as said barrier means moves toward said increased second volume; and means for temporarily increasing the flow of the driving fluid to the receiving reservoir so as to deliver a temporarily increased flow of the dispensing fluid through the orifice.

2. The pump assembly of claim 1 wherein the temporarily increasing flow means further comprises means for delivering a pulse of the driving fluid from the driving reservoir to the receiving reservoir so to deliver a pulse of the dispensing fluid through said orifice.

3. The pump assembly of claim 2 wherein the driving fluid pulse delivering means is a user-actuated means.

4. The pump assembly of claim 3 wherein the driving fluid pulse delivering means includes means for limiting the frequency of actuation thereof.

* * * * *